US008523924B2

(12) United States Patent
Meyer et al.

(10) Patent No.: US 8,523,924 B2
(45) Date of Patent: Sep. 3, 2013

(54) COLORED AND WHITE LIGHT GENERATING LIGHTING DEVICE

(75) Inventors: Jorg Meyer, Aachen (DE); Peter Lurkens, Aachen (DE); Bernd Ackermann, Aachen (DE); Andreas Tucks, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 878 days.

(21) Appl. No.: 12/302,314

(22) PCT Filed: May 22, 2007

(86) PCT No.: PCT/IB2007/051924
§ 371 (c)(1),
(2), (4) Date: Nov. 25, 2008

(87) PCT Pub. No.: WO2007/141688
PCT Pub. Date: Dec. 13, 2007

(65) Prior Publication Data
US 2009/0187234 A1    Jul. 23, 2009

(30) Foreign Application Priority Data
Jun. 2, 2006    (EP) .................................... 06114947

(51) Int. Cl.
*A61N 5/06*    (2006.01)

(52) U.S. Cl.
USPC .............................................. 607/88; 607/89

(58) Field of Classification Search
USPC ...................... 362/231; 607/88–94
See application file for complete search history.

(56) References Cited

U.S. PATENT DOCUMENTS

| 4,471,351 | A  | * | 9/1984  | Anderson ....................... 345/86 |
| 5,077,142 | A  | * | 12/1991 | Sakon et al. ................... 428/690 |
| 6,600,175 | B1 |   | 7/2003  | Baretz et al. |
| 7,651,243 | B2 | * | 1/2010  | McGuire et al. .............. 362/293 |
| 2005/0174544 | A1 |   | 8/2005  | Mazzochette |
| 2005/0189863 | A1 |   | 9/2005  | Nagatomi et al. |
| 2005/0270775 | A1 | * | 12/2005 | Harbers et al. ................ 362/231 |
| 2005/0280785 | A1 |   | 12/2005 | Beeson et al. |
| 2006/0291049 | A1 | * | 12/2006 | Juenger et al. ................ 359/443 |
| 2007/0019408 | A1 | * | 1/2007  | McGuire et al. .............. 362/231 |
| 2007/0215890 | A1 | * | 9/2007  | Harbers et al. ................. 257/98 |
| 2010/0145419 | A1 | * | 6/2010  | Fraval ............................ 607/94 |

FOREIGN PATENT DOCUMENTS

| EP | 1441395 A2    | 7/2004 |
| JP | 2004184983 A  | 7/2004 |
| JP | 2004341105 A  | 12/2004 |
| JP | 2007156270 A  | 6/2007 |
| WO | 2005022030 A2 | 3/2005 |
| WO | 2006133214 A2 | 12/2006 |

* cited by examiner

*Primary Examiner* — Bill Thomson
*Assistant Examiner* — Jeffrey Lipitz

(57) ABSTRACT

A lighting device for generating colored and white light. According to the invention the lighting device comprises at least one light source (1, 4) emitting blue or ultraviolet light and a color conversion unit (2, 5) for converting said blue or ultraviolet light into visible light comprising at least two sections (2a, 2b, 2c, 6a, 6b, 6c, 6d), at least one section (2c, 6d) of which being a transparent or translucent color converting section, said color conversion unit (2, 5) being arranged for alternately illuminating said at least two sections (2a, 2b, 2c, 6a, 6b, 6c, 6d) with said blue or ultraviolet light, said at least one color converting section containing luminescent material, wherein said luminescent material is a luminescent organic dye in a polymer matrix or a crystalline inorganic luminescent material.

13 Claims, 3 Drawing Sheets

Figure 5:
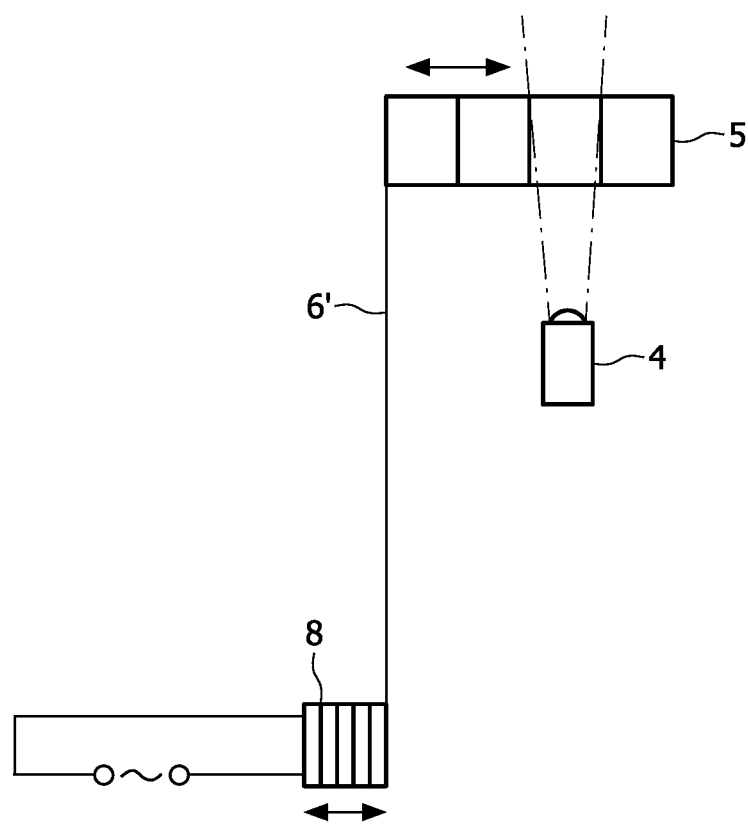

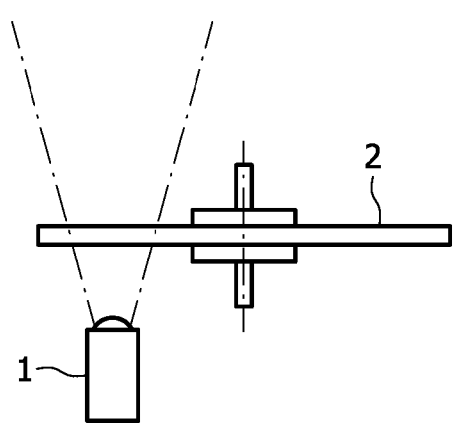
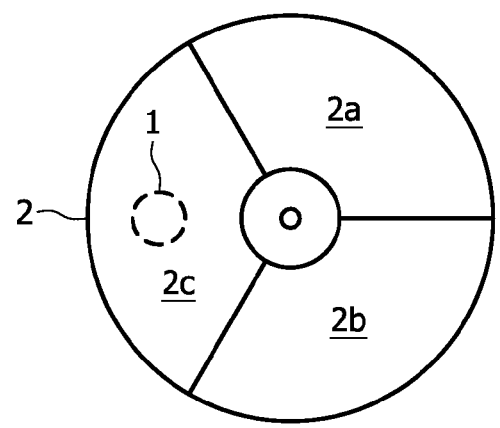
FIG. 1a          FIG. 1b
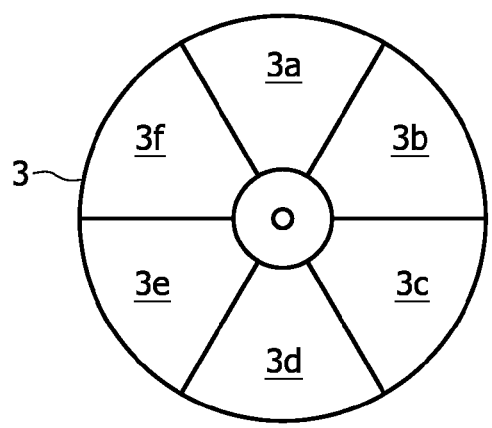
FIG. 2

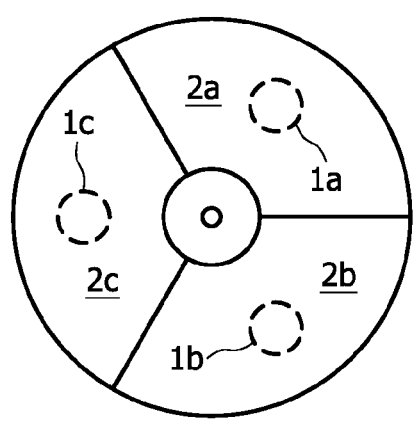
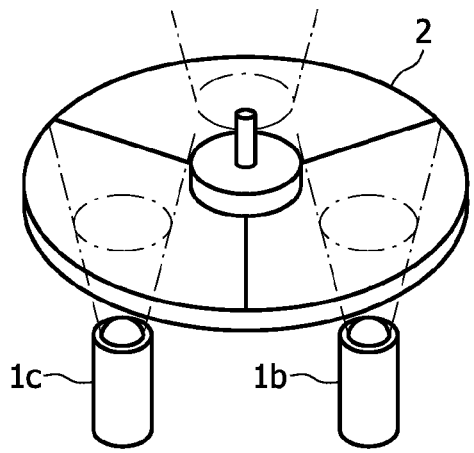
FIG. 3a      FIG. 3b
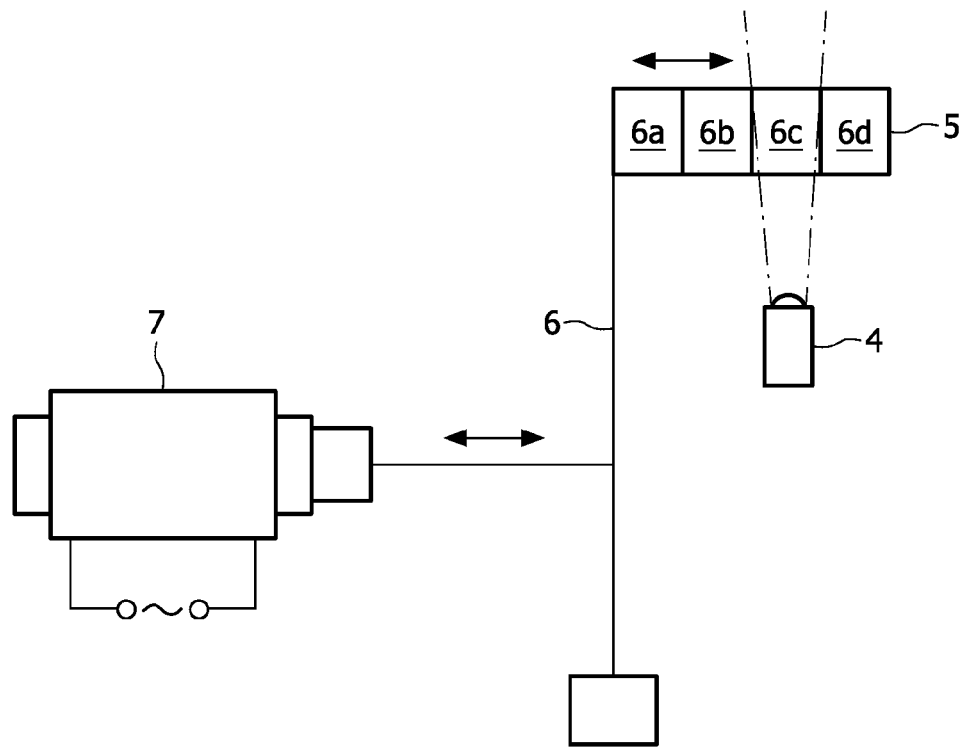
FIG. 4

COLORED AND WHITE LIGHT GENERATING LIGHTING DEVICE

The present patent application relates to a lighting device for generating colored and white light, to a method for generating colored and white light and to the use of a lighting device.

Color tunable light sources known from the art are mostly based on LED modules. Those LED modules generally rely on the emission of the primary colors red, blue, green and in some cases amber or even more primary colors by different LEDs for each color. This means that the number of LED chips is at least as high as the number of primary colors used. Usually, LED chips emitting different colors show different behavior towards driving currents, temperature and other operational parameters. This drawback may be overcome with the use of color converted blue or ultraviolet LED chips, so called phosphor converted LEDs (pc LEDs). Phosphor converted LEDs comprise a blue or ultraviolet LED light source, which illuminates a luminescent material, which for its part converts the blue or ultraviolet light of the LED into visible light having a longer wavelength, e.g. green, yellow or red light. The pc LED arrangement still has the disadvantage that several pc LEDs emitting different colors are required to obtain the desired color impression by color mixing. Moreover, spatially separated light sources require rather complex optics with precise alignment. Another constraint of pc LEDs is the possible saturation of the luminescent material, which results in luminance limitation in case of high light flux emitted by the LED.

These problems are partly solved by a lighting and display device known from JP 2004341105A. The display device comprises an ultraviolet light emitting LED, which illuminates a color wheel. On the illuminated side the color wheel is coated with a visible light reflecting film that is transmissive for ultraviolet light. The color wheel further comprises three color converting sectoral sections which convert and scatter the ultraviolet light emitted by the LED into red, green and blue light. The converted light, which is back scattered through the color wheel towards the light source is reflected by the visible light reflecting film such that a large part of the converted light can be used for the display application.

The use of a color wheel has the advantage that one light source is sufficient to generate primary colors in short subsequent time slots by cyclically moving the different color converting sectoral sections of the color wheel into the beam of the light source. The fast sequence of different primary colors is perceived as a color mixture due to the inertia of human vision. Using a single LED along with a color wheel further has the advantage that the color impression is not dependent on the unequal behavior of different LEDs towards driving currents, temperatures and other parameters.

However, the display device known from JP 2004341105A has the drawback that the color wheel has a complex design featuring color converting sections on the one hand and a visible light reflecting film on the other hand. Further, not the entire light flux emitted by the LED can be used for the display application as the ultraviolet light coming from the LED is scattered in the color converting sections and partly reflected by the visible light reflecting film.

It is thus an object of the invention to provide a lighting device for generating colored light of any desired color having high spectral purity and stability or white light having a high luminance. The lighting device should further comprise a color conversion unit having a simple and thus cost effective design. Another object of the present patent application is to provide a lighting device, which shows a high luminous efficiency.

These and other objects are solved by a lighting device for generating colored and white light, comprising at least one light source emitting blue or ultraviolet light, a color conversion unit for converting said blue or ultraviolet light into visible light comprising at least two sections, at least one section of which being a transparent or translucent section, said color conversion unit being arranged for alternately illuminating said at least two sections with said blue or ultraviolet light, said at least one section containing luminescent material, wherein said luminescent material is a luminescent organic dye in a polymer matrix or a crystalline inorganic luminescent material.

The color conversion unit of the lighting device according to the invention comprises transparent luminescent material, which allows for highly efficient color conversion of the ultraviolet or blue light emitted by the light source and securely avoids beam deflection or scattering decreasing luminous efficiency of the lighting device. Using a transparent luminescent material also ensures a minimum etendue, which is important for spotlight and projection applications. The color converting sections comprising luminescent materials can either be translucent (partly transmitting light emitted by the light source, so-called primary light) or convert the primary light completely into visible light with a different wavelength.

In contrast to conventional luminescent materials organic dyes in a polymer matrix as well as crystalline inorganic luminescent material feature a high quantum efficiency. As radiationless relaxation of the excited states in the irradiated dye molecules or the inorganic crystal is highly unlikely the irradiated light emitted by the light source is almost entirely converted into visible light. Further, the color conversion unit is characterized by a simple and thus cost-effective design as a special coating of its surfaces is not needed.

According to a first embodiment of the invention the light source is a light emitting diode (LED). The main advantage of an LED is that it has a long service live and a high degree of energetic efficiency. LEDs emitting blue or ultraviolet light are readily available on the market. As only a single LED is used the color impression of the light generated by the lighting device is therefore independent of temperature and driving current.

According to another embodiment of the invention the luminescent organic dye is a dye comprising Perylene tetracarbonic acid. These innovative organic dyes can be produced with a large variety of color converting characteristics. Correspondingly, the blue or ultraviolet light emitted by the light source can be converted into a large number of colors with high spectral purity and luminance.

For example, the at least one color converting section of the color conversion unit can be arranged to convert said blue or ultraviolet light into green light. In this case the inorganic luminescent material contains $SrSi_2O_2N_2$:Eu and/or LuAG:Ce (Luthetium-Aluminum-Garnet doped with Cerium). The color converting section of the color conversion unit may also be arranged to convert the blue or ultraviolet light emitted by the light source into red light. In this case the inorganic luminescent material contains CaS:Eu and/or $CaAlSiN_3$:Eu.

In a further embodiment, the inorganic luminescent material exhibits a density of more than 97% of its theoretical density as a single crystal material in order to further reduce the amount of radiationless relaxation of the excited states in the irradiated inorganic luminescent material by reducing scattering effects within the luminescent material resulting in a shorter light path of converted light within the luminescent material before leaving the luminescent material. The high density can be generated for example by pressing the materials at high pressure.

According to another embodiment of the invention the light source emits blue light and the color conversion unit comprises at least one transparent section. In the case of a blue light emitting light source, e.g. a blue LED, the light can directly be used for color mixture so that a complete color conversion may not be necessary. The transparent section can be made of glass or a transparent polymer, such as polycarbonate.

According to another advantageous embodiment of the invention the color conversion unit comprises three sections being arranged so as to periodically convert said blue or ultraviolet light into red, green and blue light. By generating the primary colors red, green and blue the lighting device according to the invention may be used for generating a wide spectrum of colors, especially for illumination or display applications. In the case of an UV light source, the color conversion unit may comprise a transparent section and two color converting sections being arranged so as to convert the UV light into yellow and blue light, respectively. In the case of a blue light source the color conversion unit may comprise a transparent section and two color converting sections being arranged so as to convert the blue light into red and green light, respectively. In the case of a blue light source the color conversion unit may also comprise only two sections, one of which being a transparent or translucent section and the other be a color converting section arranged for converting the blue light into yellow light.

According to another embodiment of the invention the color conversion unit is designed as a rotational oscillator to be rotated with a rotational frequency, especially a color wheel comprising at least two sectoral sections, at least one of which being a color converting section. An advantage of a rotational oscillator, especially a color wheel, is that it may also serve as a cooling fan for the lighting device due to the boundary layer of the air on it surface. Further cooling fan elements can be attached to the axis of the rotative oscillator.

Preferably, the color wheel comprises at least four sections perform more than one color cycle per revolution. Here, a color cycle denotes the fraction of one revolution required to emit light comprising all different colors provided by the color wheel. As an example, if there are two sections emitting blue light and two sections emitting yellow light and the sections are arranged in a blue/yellow/blue/yellow sequence, the color wheel performs two color cycles per revolutions in contrast to a color wheel where only two sections (one blue, one yellow) are present. In the latter case, the color wheel would perform only one color cycle per revolution. By realizing more than one color cycle per revolution color break-up effects may be reduced or, as an alternative, the required rotational frequency of the color wheel may be reduced.

According to another advantageous embodiment of the invention the contact surfaces between the sectoral sections of the color wheel are provided with a reflective coating. This will avoid leakage of light from one section to the other, as may be caused by light guiding phenomena.

According to another embodiment of the invention the number of light sources corresponds to the number of sectoral sections of the color wheel, wherein the light sources are arranged so as to simultaneously illuminate all sectoral sections of the color wheel. This allows for increasing the total light flux and decreasing color break-up effects by decreasing the color variation amplitude in the resulting light beam.

The color wheel may be produced in different ways. For example, the sectoral sections of the color wheel may be joined by gluing. In the case of the use of luminescent organic dyes in a polymer matrix the color wheel may be also produced by molding the polymers containing the respective dyes together in a single compact shape.

According to another embodiment of the invention the color conversion unit is designed as a linear oscillator to be oscillated with an oscillation frequency. The linear oscillator may comprise a piezo actuator or a solenoid.

The light source of the lighting device may be a continuously emitting light source. It may also be a pulsed light source. In the latter case the lighting device preferably comprises an electronic control unit arranged to synchronize the pulse pattern of the light source with the alternating frequency of the color conversion unit, e.g. the color wheel, so as to generate the desired shade of color.

Another aspect of the patent application is a method for generating colored light, comprising at least one light source emitting blue or ultraviolet light a color conversion unit for converting said blue or ultraviolet light into visible light, said color conversion unit comprising at least two sections, at least one section of which being a color converting section, said at least one color converting section containing luminescent material, said luminescent material being a luminescent organic dye in a polymer matrix or a crystalline inorganic luminescent material, wherein said at least two sections are alternately illuminated with said blue or ultraviolet light.

According to an embodiment of the method according to the invention the light source is a pulsed light source and the pulse pattern of said pulsed light source is synchronized with the alternating frequency of said color conversion unit so as to generate the desired shade of color, wherein the alternating frequency of said color conversion unit is adapted to the pulse pattern of said pulsed light source or the pulse pattern of said pulsed light source is adapted to the alternating frequency of said color conversion unit.

Another aspect of the patent application is the use of a lighting device of claim 1 as a color tunable light source for general illumination or in medical, artistic and photographic applications. A lighting device providing light with comprising UV light can be used for illumination purposes where fluorescent effects are desired. Another aspect of the patent application is the use of a lighting device of claim 1 in a projection device.

Yet, another aspect of the patent application is the use of a lighting device of claim 1 having a UV light source as a means for medical treatment of skin defects and skin diseases, particularly psoriasis.

These and other aspects of the present patent application will be come apparent from an elucidated with reference to the following figures.

FIGS. 1a, b illustrates a side view and a top view of a lighting device according to the invention comprising a light source and a color conversion unit having a rotative oscillator, FIG. 2 illustrates a top view of another embodiment of the rotative oscillator of FIG. 1, FIG. 3 a, b illustrates a top view and a perspective view of another embodiment of the lighting device of FIG. 1 featuring three light sources, FIG. 4 illustrates a side view of a lighting device according to the invention comprising a light source and a color conversion unit having a linear oscillator and FIG. 5 illustrates a side view of the lighting device of FIG. 4 featuring another embodiment of the linear oscillator.

FIG. 1a illustrates a side view of a lighting device according to the invention comprising a light source and a color conversion unit. Presently, the light source is designed as a blue LED 1. However, the invention is not limited to LEDs. The light source can also be designed as a blue light emitting laser, e.g. a blue semiconductor laser or an ArF* laser, or a gas discharge lamp. The color conversion unit is presently designed as a color wheel 2 driven by a motor (not shown) to rotate the color wheel with a rotational frequency. In another embodiment, the rotational frequency may be varied during the use of the lighting device. Yet, it may be designed as any other suitable rotational as well.

The color wheel 2 presently comprises two color converting sectoral sections 2a, 2b and a transparent section 2c. The color converting sectoral sections 2a, 2b each comprise a polymer matrix containing a luminescent organic dye. Preferably, the luminescent organic dye is a dye on the basis of Perylene tetracarbonic acid. The organic dye of sectoral section 2a converts the blue light emitted by LED 1 into red light whereas the organic dye of sectoral sections 2b converts the blue light into green light. As an alternative, the color converting sections 2a, 2b each may comprise a crystalline inorganic luminescent material, sintered into a transparent or translucent ceramic body. In the case of sectoral section 2a which converts the blue light into green light the inorganic luminescent material may be $SrSi_2O_2N_2$:Eu and/or LuAG: Ce. Sectoral section 2b which converts the blue light into red light may contain CaS:Eu and/or $CaAlSiN_3$:Eu as the crystalline inorganic luminescent material. Sectoral section 2c is made up of a transparent material, such as glass or a transparent polymer, e.g. Polycarbonate. Preferably, the contact surfaces between the sectoral sections 2a, 2b, 2c of color wheel 2 are provided with a reflective coating. By using reflective coatings between the respective sectoral sections crossover effects are securely avoided Having two color converting sectoral sections 2a, 2b converting the blue light of the LED into red or green light, respectively, and a transparent section 2c being completely transparent for blue light the color wheel 2 covers a full color cycle and thus can be used for a plurality of display or illumination applications.

The lighting device of FIG. 1a further comprises an electronic control unit (not shown) which controls the driving current of the LED 1 and the rotational frequency of the color wheel 2. For example, LED 1 is driven by a pulsed driving current such that it emits a pulsed light beam. The pulse length and the pulse frequency may be adapted to the rotational frequency in such way that the resulting light beam behind the color wheel yields white light, taking into account the inertia and wavelength dependent sensitivity of human vision. By increasing the pulse length of those pulses that, for example, pass through the transparent sectoral section 2c of the wheel 2 the color impression may be easily shifted towards the blue. It shall be understood that the color impression can also be controlled by altering the angular extent of the individual sectoral sections.

In another embodiment of the lighting device according to the invention (not shown) the light source may be designed as an ultraviolet light emitting LED or a UV laser, e.g. a KrF* laser. It shall be understood that in this case transparent section 2c of the color wheel 2 has to be replaced by a color converting section, which, for example, converts the pulsed UV light of the laser into blue light.

FIG. 2 shows a top view of another embodiment of the color wheel of FIG. 1b.

In contrast to the color wheel 2 of FIG. 1b color wheel 3 comprises two color converting sections 3a, 3d converting blue light into red light, two color converting sections 3b, 3e converting blue light into green light and two transparent sections 3c, 3f. Color wheel 3 thus covers two color cycles per revolution. This has the advantage that break-up effects are strongly reduced or, as an alternative, the required rotational frequency of the color wheel may be reduced. As in the case of color wheel 2 of FIG. 1b the contact surfaces between the sectoral sections 3a-3f of color wheel 3 are preferably covered with a reflecting coating.

FIG. 3a shows a top view of another embodiment of the lighting device according to the invention.

The lighting device of FIG. 3a comprises three different LEDs 1a, 1b, 1c each emitting blue light. The lighting device of FIG. 3a further comprises a color wheel 2 which comprises three sectoral sections 2a, 2b, 2c. Sectoral sections 2a, 2b are designed to convert the blue light into red or green light, respectively, whereas sectoral sections 2c is completely transparent for blue light. The blue LEDs 1a, 1b, 1c are a spaced apart from each other in a 120° angular distance, respectively, so as to simultaneously illuminate the three sectoral sections 2a, 2b, 2c of color wheel 2. This allows for increasing the total light flux while decreasing color break-up effects by decreasing the color variation amplitude in the resulting light beam.

FIG. 4 illustrates a side view of a lighting device according to the invention featuring a color conversion unit driven by a linear oscillator.

In detail, the lighting device of FIG. 4 comprises a blue LED 4 as the light source and a color conversion unit 5, which for its part comprises three color converting sections 6a, 6b, 6c and a transparent section 6d. In contrast to the color wheel of FIG. 1 to 3 sections 6a-6d of color conversion unit 5 are arranged adjacent to each other in a linear arrangement. Further, color conversion unit 5 is coupled to a mechanical resonator 6 in order to drive the color conversion unit 5 with an oscillating frequency. By realizing more than one color cycle per oscillation, a more homogeneous color impression of the light emitted from different sections of the conversion unit will be obtained. Alternatively, the oscillation frequency can be decreased by increased number of color converting sections 6a-6d to obtain the same color impression as obtained with a lower number of color conversion sections at higher frequencies. Presently, mechanical resonator 6 is stimulated by an electromagnetic actuator (solenoid) 7 being connected to an alternating current supply.

When stimulated by the solenoid 7 the mechanical resonator and the color conversion unit 5 being coupled to the resonator 6 perform a linear oscillating movement such that the blue light emitted by LED 4 successively illuminates color converting sections 6a, 6b, 6c and transparent section 6d. Like a color wheel the color conversion unit 5 generates a fast sequence of different colors, which is perceived as a color mixture due to the inertia of human vision.

FIG. 5 shows a side view of another lighting device featuring a different color conversion unit driven by a linear oscillator.

In contrast to the lighting device of FIG. 4 mechanical resonator 6' is stimulated by a piezo actuator 8 in order to drive the color conversion unit 5 with an oscillating frequency, which is connected to an alternating voltage supply.

While there have been shown and described and pointed out fundamental novel features of the invention as applied to a preferred embodiment thereof, it will be understood that various omissions and substitutions and changes in the form and details of the devices and methods described may be made by those skilled in the art without departing from the spirit of the invention. For example, it is expressly intended that all combinations of those elements and/or method steps, which perform substantially the same function in substantially the same way to achieve the same results, are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto. It should also be recognised that any reference signs shall not be constructed as limiting the scope of the claims.

The invention claimed is:

1. Lighting device for generating colored and white light, comprising:
    at least one light source emitting blue or ultraviolet light,
    a color conversion unit for converting said blue or ultraviolet light into visible light comprising at least two sections, at least one section of which being a color converting section, said color conversion unit being arranged for alternately illuminating said at least two sections with said blue or ultraviolet light, said at least one color converting section containing luminescent material,
    wherein said luminescent material is a crystalline inorganic luminescent material formed into a ceramic body, and wherein said luminescent material avoids beam deflection of light incident on the luminescent material and is substantially non-scattering, and
    wherein said inorganic luminescent material exhibits a density of more than 97% of its theoretical density as a single crystal material.

2. The lighting device of claim 1, wherein said light source is a light emitting diode.

3. The lighting device as claimed in claim 1, wherein said color converting section is arranged to convert said blue or ultraviolet light into green light and contains $SrSi_2O_2N_2$:Eu and/or LuAG:Ce as the crystalline inorganic luminescent material or wherein said color converting section is arranged to convert said blue or ultraviolet light into red light and contains CaS:Eu and/or $CaAlSiN_3$:Eu as the crystalline inorganic luminescent material.

4. The lighting device as claimed in claim 1, wherein said color conversion unit is designed as a rotational oscillator to be rotated with a rotational frequency or linear oscillator to be oscillated with an oscillation frequency.

5. The lighting device of claim 4, wherein said rotational oscillator is a color wheel to be rotated with a rotational frequency comprising at least two sectoral sections, at least one of which being a transparent or translucent color converting section.

6. The lighting device of claim 5, wherein said color wheel comprises at least four sections to perform more than one color cycle per revolution.

7. The lighting device of claim 5, wherein the contact surfaces between said sectoral sections are provided with a reflective coating.

8. The lighting device of claim 4, wherein said linear oscillator comprises a piezo actuator or a solenoid.

9. The lighting device as claimed in claim 1, wherein said light source is a pulsed light source and the lighting device further comprises a electronic control unit arranged to synchronize the pulse pattern of said pulsed light source with the alternating frequency of said color conversion unit so as to generate the desired shade of color.

10. A method for generating colored and white light, comprising
    at least one light source emitting blue or ultraviolet light,
    providing a color conversion unit for converting said blue or ultraviolet light into visible light, said color conversion unit comprising at least two sections, at least one section of which being a color converting section, said at least one color converting section containing luminescent material, said luminescent material being a luminescent organic dye in a polymer matrix or a crystalline inorganic luminescent material formed into a ceramic body, said luminescent material being configured to avoid beam deflection of light incident on the luminescent material and to be substantially non-scattering, and alternately illuminating said at least two sections with said blue or ultraviolet light, and
    wherein said inorganic luminescent material exhibits a density of more than 97% of its theoretical density as a single crystal material.

11. The method of claim 10, wherein the light source is a pulsed light source and the pulse pattern of said pulsed light source is synchronized with the alternating frequency of said color conversion unit so as to generate the desired shade of color.

12. The lighting device of claim 1, wherein the color converting section partly transmits light emitted by the light source.

13. The lighting device of claim 1, wherein the luminescent material is transparent.

* * * * *